United States Patent [19]
Bäckström et al.

[11] Patent Number: 5,952,008
[45] Date of Patent: *Sep. 14, 1999

[54] PROCESSES FOR PREPARING COMPOSITIONS FOR INHALATION

[75] Inventors: Kjell Göran Erik Bäckström; Carl Magnus Olof Dahlbäck, both of Lund; Peter Edman, Bjärred; Ann Charlotte Birgit Johansson, Lund, all of Sweden

[73] Assignee: AB Astra, Sodertalje, Sweden

[*] Notice: This patent is subject to a terminal disclaimer.

[21] Appl. No.: 08/858,122

[22] Filed: May 19, 1997

Related U.S. Application Data

[60] Continuation of application No. 08/468,418, Jun. 6, 1995, abandoned, which is a division of application No. 08/265, 237, Jun. 23, 1994, abandoned.

[30] Foreign Application Priority Data

Jun. 24, 1993 [SE] Sweden ................................ 9302198
Feb. 4, 1994 [SE] Sweden ................................ 9400371

[51] Int. Cl.⁶ ............................. A61K 9/14; A61K 9/72; A61K 38/16; A61K 47/12
[52] U.S. Cl. ......................... 424/499; 424/46; 424/489; 424/502; 424/85.2; 424/434; 514/2; 514/3; 514/951; 530/399
[58] Field of Search .............................. 424/46, 489, 499, 424/502, 85.2, 434; 514/2, 3, 8, 12, 54, 58, 800, 802, 805–890, 350, 359, 951; 530/303, 306, 307, 308, 311, 313, 315, 398, 399; 930/50

[56] References Cited

U.S. PATENT DOCUMENTS

| | | |
|---|---|---|
| 3,014,844 | 12/1961 | Thiel . |
| 4,524,769 | 6/1985 | Wetterlin ........................... 128/203.15 |
| 4,534,345 | 8/1985 | Wetterlin ........................... 128/203.15 |
| 4,548,922 | 10/1985 | Carey et al. ............................. 514/4 |
| 4,613,500 | 9/1986 | Suzuki et al. ......................... 424/85.4 |
| 4,668,218 | 5/1987 | Virtanen .................................. 604/58 |
| 4,690,952 | 9/1987 | Kagatani et al. ......................... 514/11 |
| 4,746,508 | 5/1988 | Carey et al. ............................. 424/88 |
| 4,788,221 | 11/1988 | Kagatani et al. ......................... 514/12 |

(List continued on next page.)

FOREIGN PATENT DOCUMENTS

| | | |
|---|---|---|
| 43556/93 | 1/1994 | Australia . |
| 0 023 359 | 7/1980 | European Pat. Off. . |
| 0 055 041 | 12/1981 | European Pat. Off. . |
| 0 122 036 | 10/1984 | European Pat. Off. . |
| 0 200 383 | 4/1986 | European Pat. Off. . |
| 0 225 189 | 11/1986 | European Pat. Off. . |
| 0 272 097 | 6/1988 | European Pat. Off. . |
| 0 360 340 | 3/1990 | European Pat. Off. . |
| 0 455 463 | 11/1991 | European Pat. Off. . |

(List continued on next page.)

OTHER PUBLICATIONS

Olanoff et al., "Method to Enhance Intranasal Peptide Delivery", in "Controlled–Release Technology Pharmaceutical Applications", Lee et al., Ed., Published 1987 by The American Chemical Society, pp. 301–309.

Mishima et al., "Studies on the Promoting Effects of Medium Chain Fatty Acid Salts on the Nasal Absorption of Insulin in Rats", J. Pharm. Sci., vol. 10, issued 1987, pp. 624–631.

(List continued on next page.)

Primary Examiner—Robert H. Harrison
Attorney, Agent, or Firm—Fish & Richardson P.C.

[57] ABSTRACT

A pharmaceutical composition including a mixture of active compounds (A) a pharmaceutically active polypeptide, and (B) an enhancer compound which enhances the systemic absorption of the polypeptide in the lower respiratory tract of a patient, the mixture being in the form of a dry powder for inhalation in which at least 50% of the total mass of the active compounds cons

U.S. PATENT DOCUMENTS

| | | |
|---|---|---|
| 4,847,298 | 4/1989 | Alexander . |
| 4,895,719 | 1/1990 | Radhakrishnan . |
| 4,900,730 | 2/1990 | Miyauchi .................................. 514/12 |
| 4,907,583 | 3/1990 | Wetterlin et al. .................. 128/203.15 |
| 4,959,358 | 9/1988 | Carey et al. ............................ 514/171 |
| 4,963,367 | 10/1990 | Ecanow . |
| 4,994,439 | 2/1991 | Longenecker . |
| 5,006,343 | 4/1991 | Benson . |
| 5,011,678 | 4/1991 | Wang . |
| 5,118,494 | 6/1992 | Schultz . |
| 5,122,127 | 6/1992 | Stanley . |
| 5,122,376 | 6/1992 | Aliverti . |
| 5,179,079 | 1/1993 | Hansen et al. .............................. 514/4 |
| 5,192,548 | 3/1993 | Velasquez et al. ...................... 424/443 |
| 5,200,393 | 4/1993 | Weiner . |
| 5,202,129 | 4/1993 | Samejima et al. ...................... 424/489 |
| 5,254,330 | 10/1993 | Ganderton et al. ........................ 424/46 |
| 5,260,306 | 11/1993 | Boardman et al. ..................... 514/291 |
| 5,284,656 | 2/1994 | Platz et al. .............................. 424/435 |
| 5,288,498 | 2/1994 | Stanley et al. .......................... 424/440 |
| 5,341,800 | 8/1994 | Clark et al. ........................ 128/203.15 |
| 5,348,730 | 9/1994 | Greenleaf . |
| 5,354,562 | 10/1994 | Platz et al. .............................. 424/489 |
| 5,364,838 | 11/1994 | Rubsamen .................................. 514/3 |
| 5,376,386 | 12/1994 | Ganderton et al. ..................... 424/499 |
| 5,384,133 | 1/1995 | Boyes et al. ............................ 424/501 |
| 5,419,315 | 5/1995 | Rubsamen . |
| 5,437,271 | 8/1995 | Hodson et al. ..................... 128/203.15 |
| 5,482,032 | 1/1996 | Smith et al. ....................... 128/203.15 |
| 5,482,706 | 1/1996 | Igari et al. . |
| 5,506,203 | 4/1996 | Baeckstroem et al. ...................... 514/4 |
| 5,514,670 | 6/1996 | Friedman . |
| 5,518,998 | 5/1996 | Baeckstroem et al. ...................... 514/3 |
| 5,658,878 | 8/1997 | Backstrom et al. ......................... 514/3 |
| 5,707,644 | 1/1998 | Illum ....................................... 424/434 |
| 5,747,445 | 5/1998 | Backstrom et al. ......................... 514/4 |
| 5,830,853 | 11/1998 | Backstrom et al. ......................... 514/4 |
| 5,858,968 | 1/1999 | Weiner et al. .............................. 514/3 |

FOREIGN PATENT DOCUMENTS

| | | |
|---|---|---|
| 261 096 A1 | 10/1988 | Germany . |
| 8007820 | 11/1986 | Sweden . |
| 837465 | 6/1960 | United Kingdom . |
| 1 527 605 | 10/1976 | United Kingdom . |
| 88/09163 | 12/1988 | WIPO . |
| 90/07333 | 4/1990 | WIPO . |
| 90/04962 | 5/1990 | WIPO . |
| 91/16038 | 10/1991 | WIPO . |
| 91/16882 | 11/1991 | WIPO . |
| 91/16929 | 11/1991 | WIPO . |
| 92/08446 | 5/1992 | WIPO . |
| 93/25198 | 12/1993 | WIPO . |
| 92/07514 | 4/1994 | WIPO . |
| 94/22461 | 10/1994 | WIPO . |
| 95/00151 | 1/1995 | WIPO . |

OTHER PUBLICATIONS

Lee et al., "Intranasal Bioavailability of Insulin Powder Formulations: Effect of Permeation Enhancer–to–Protein Ratio", Journal of Pharmaceutical Sciences, vol. 80, No. 8, issued Aug. 1991, pp. 725–729.
Schipper et al., "Nasal Insulin Delivery with Dimethyl–beta–Cyclodextrin as an Absorption Enhancer in Rabbits: Powder More Effective than Liquid Formulations", Pharmaceutical Research, vol. 10, No. 5, issued 1993, pp. 682–686.
Chien et al., "Intranasal Drug Delivery For Systemic Medications", CRC Critical Reviews in Therapeutic Drug Carrier Systems 4:67–194, 1987.
Eppstein et al., "Alternative Delivery Systems for Peptides and Proteins As Drugs", CRC Critical Reviews in Therapeutic Drug Carrier Systems 5:99–139, 1988.
O'Hagan et al., "Absorption of Peptides and Proteins from the Respiratory Tract and the Potential for Development of Locally Administered Vaccine", Critical Reviews in Therapeutic Drug Carrier Sys 7:35–97, 1990.
Remington's Pharmaceutical Science, 18th edn., p. 1079 (1990).
Longenecker et al., Effects of Sodium Taurodihydrofusidate on Nasal Absorption of Insulin in Sheep, *J. Pharm. Sci.,* 76(5):351–355 (1987).
Mizgala et al., Renal Handling of Phosphate, *Physiological Reviews,* 65(2):431–466 (1985).
Salzman et al., Intranasal Aerosolized Insulin Mixed–Meal Studies and Long–term Use in Type I Diabetes, *The New England Journal of Medicine,* 312:1078–1084, 1985.
Zingg et al., Transhepatic Absorption and Biliary Excretion of Insulin, *Can. J. Physiol. Pharmacol.,* 65:1982–1987 (1987).
Ruin, Sydsvenska (Dagbladet), Monday, Jun. 12, 1989, Diabetics May Not Need Their Insulin Shots.
Almer et al., Diabetes Res. and Clin. Pract. 5:S163 (1988).
Björk, Acta Univ. Uppsala, Comprehensive Summaries of Uppsala Dissertations from the Faculty of Pharmacy 103 (1993).
Timsina et al., Drug Delivery to the Respiratory Tract Using Dry Powder Inhalers, Int. J. Pharmaceutics 101:1–13 (1994).
Komada et al., Intratracheal Delivery of Peptide and Protein Agents: Absorption from Solution and Dry Powder by Rat Lung, J. Pharm. Sci. 83:863–867 (1994).
Lee et al., Intranasal Bioavailability of Insulin Powder Formulations: Effect of Permeation Enhancer–to–Protein Ratio, J. Pharm Sci. 80:725–729 (1991).
Schipper et al., Nasal Insulin Delivery with Dimethyl–β–Cyclodextrin as an Absorption Enhancer in Rabbits: Powder More Effective than Liquid Formulations, Pharm. Res. 10:682–686 (1993).
Lee et al., Mucosal Penetration Enhancers for Facilitation of Peptide and Protein Drug Absorption, Critical Rev. Therapeut. Drug Carrier Systems 8:91–192 (1991).
Wearly, Recent Progress in Protein and Peptide Delivery by Noninvasive Routes, Critical Rev. Therapeut. Drug Carrier Systems 8:331–394 (1991).
Laube et al., Preliminary Study of the Efficacy of Insulin Aerosol Delivered by Oral Inhalation in Diabetic Patients, JAMA 269:2106–2109 (1993).
Dahlbäck et al., Regional Administration of Drugs to the Rabbit Respiratory Tract, Effects on Absorption, J. Aerosol Medicine 1:222–223 (1988).
Yoshida et al., Absorption of Insulin Delivered to Rabbit Trachea Using Aerosol Dosage Form, J. Pharma. Sci. 68:670–671 (1979).
Damasy et al., Diabetes Res. and Clin. Pract. 5:S163 (1988).
Chandler et al., Nasal Absorption in Rats. II. Effect of Enhancers on Insulin Absorption and Nasal Histology, Int. J. Pharmaceutics 76:61–70 (1991).
Hirai et al., Effect of Surfactants on the Nasal Absorption of Insulin in Rats, Int. J. Pharmaceutics 9:165–172 (1981).
Gordon et al., Nasal Absorption of Insulin: Enhancement by Hydrophobic Bile Salts, Proc. Natl. Acad. Sci. USA 82:7419–7423 (1985).
Moses et al., Insulin Administered Intranasally as an Insulin–Bile Salt Aerosol, Diabetes 32:1040–47 (1983).

Wigley et al., Insulin Across Respiratory Mucosae by Aerosol Delivery, Diabetes 20:552–556 (1971).

Cutie et al., The Role of Dispersing Agents in Inhalation and Intranasal Aerosol Suspensions, Aerosol. Age 30:52–54 (1985).

Allenby et al., The Absorption of Insulin Across the Respiratory Tract of the Guinea–Pig (U), The Aerosol Society, Fourth Annual Conference 1990, pp. 129–134.

Aungst and Rogers, Comparison of the Effects of Various Transmucosal Absorption Promoters on Buccal Insulin Delivery, Int. J. Pharm. (Netherlands), 1989, 53/3, 227–235.

Björk, Starch Microspheres as a Nasal Delivery System for Drugs, Comprehensive Summaries of Uppsala Dissertations from the Faculty of Pharmacy 103, 1993.

Björk and Edman, Degradable Starch Microspheres as a Nasal Delivery System for Insulin, Int. J. Pharm. 47:233–238, 1988.

Brange et al., Monomeric Insulins and Their Experimental and Clinical Implications, Diabetes Care 13:923–954, 1990.

Edman and Björk, Routes of Delivery: Case Studies, Advanced Drug Delivery Reviews 8:165–177, 1992.

Igawa et al., Effect of Absorption Promoters in Intranasal Administration of Human Fibroblast Interferon as a Powder Dosage Form in Rabbits, Chem. Pharm. Bull. 37:418–421, 1989.

Komada et al., Intratracheal Delivery of Peptide and Protein Agents: Absorption from Solution and Dry Powder by Rat Lung, J. Pharm. Sci. 83:863–867, 1994.

Lasker, The Diabetes Control and Complications Trial, N. Engl. J. Med. 329:1035–1036, 1993.

Laube et al., Preliminary Study of the Efficacy of Insulin Aerosol Delivered by Oral Inhalation in Diabetic Patients, JAMA 269:2106–2109, 1993.

Lee et al., Intranasal Bioavailability of Insulin Powder Formulations: Effect of Permeation Enhancer–to–Protein Ratio, J. Pharm. Sci. 80:725–729, 1991.

Mishima et al., Studies on the Promoting Effects of Medium Chain Fatty Acid Salts on the Nasal Absorption of Insulin in Rats, J. Pharma –Dyn. 10:624–631, 1987.

Morita et al., Effects of Various Absorption Promoters on Pulmonary Absorption of Drugs with Different Molecular Weights, Biol. Pharm. Bull. 16:269:262, 1993.

Nagai et al., Powder Dosage Form of Insulin for Nasal Administration, J. Controlled Release 1:15–22, 1984.

"Diabetes Mellitus", Ch. VI in Scientific American Medicine, Scientific American, Inc., Apr. 1993.

The Diabetes Control and Complications Trial Research Group, The Effect of Intensive Treatment of Diabetes on the Development . . . Complications in Insulin–Dependent Diabetes Mellitus, N. Engl. J. Med. 329:977–86, 1993.

Pontiroli et al., Nasal Administration of Glucagon and Human Calcitonin to Healthy Subjects: a Comparison of Powders and Spray Solutions and of Different Enhancing Agents, Eur. J. Clin. Pharmacol. 37:427–430, 1989.

Schipper et al., Nasal Insulin Delivery with Dimethyl–β–Cyclodextrin as an Absorption Enhancer in Rabbits: Powder More Effective than Liquid Formulations, Pharmaceutical Research 10:682–686, 1993.

Selam and Charles, Devices for Insulin Administration, Diabetes Care 13:955–979, 1990.

Touitou and Rubenstein, Targeted Enteral Delivery of Insulin to Rats, Int. J. Pharm. (Amst.), 30(2–3), 1986, 95–100.

Wigley et al., Insulin Across Respiratory Mucosae by Aerosol Delivery, Diabetes 20:552–556, 1971.

Zinman, Medical Intelligence—The Physiologic Replacement of Insulin, N. Engl. J. Med. 321:363–370, 1989.

Transport of mannitol across Caco-2 cell monolayer in presence of Na-caprate (10-16 mM)

A. Na-caprate
B. Na-caprate/insulin (1:3 w/w)

PROCESSES FOR PREPARING COMPOSITIONS FOR INHALATION

This is a continuation of application Ser. No. 08/468,418, filed Jun. 6, 1995, abandoned; which is a divisional of application Ser. No. 08/265,237, filed Jun. 23, 1994, abandoned.

This invention relates to methods and compositions for delivery of medically useful peptides and proteins.

BACKGROUND OF THE INVENTION

Although the advent of recombinant DNA technology has resulted in a rapidly expanding list of peptide-based drugs, a major drawback of peptide-based therapy has acutely hampered realization of the full potential of this field: in general, peptide-based drugs cannot be orally administered in effective doses, since they are rapidly degraded by enzymes in the gastrointestinal tract before they can reach the bloodstream. Unless the polypeptide of interest can be altered to make it relatively resistant to such enzymes, the only practical method of delivering the drug is likely to be a parenteral route, such as by intravenous, intramuscular, or subcutaneous injection. Administration by other parenteral routes (e.g., by absorption across nasal, buccal or rectal membranes, or via the lung) has met with limited success.

SUMMARY OF THE INVENTION

It has been found that when a peptide or protein (hereinafter collectively referred to as polypeptides) is combined with an appropriate absorption enhancer and is introduced into the lung in the form of a powder of appropriate particle size, it readily enters the pulmonary circulation by absorption through the layer of epithelial cells in the lower respiratory tract. This is conveniently accomplished by inhalation of the powder from an inhaler device which dispenses the correct dose of powdered polypeptide/enhancer in a particle size which maximizes deposition in the lower respiratory tract, as opposed to the mouth and throat. (For ease of reference, the polypeptide and enhancer are hereinafter collectively referred to as the "active compounds"). To accomplish this preferential delivery into the lung, as much as possible of the active compounds should consist of particles having a diameter less than approximately 10 $\mu$m (e.g., between 0.01–10 $\mu$m, and ideally between 1–6 $\mu$m). In preferred embodiments, at least 50% (preferably at least 60%, more preferably at least 70%, still more preferably at least 80%, and most preferably at least 90%) of the total mass of active compounds which exits the inhaler device consists of particles within the desired diameter range.

The invention thus includes a pharmaceutical composition containing a mixture of active compounds (A) a pharmaceutically active polypeptide and (B) an enhancer compound which enhances the systemic absorption of the polypeptide in the lower respiratory system (preferably the lungs) of a patient, the mixture being in the form of a dry powder suitable for inhalation, in which at least 50% of the total mass of active compounds (A) and (B) consists of primary particles having a diameter less than or equal to about 10 microns. The primary particles may be packaged as such, or may optionally be formed into agglomerates, which then are substantially deagglomerated prior to entry into the respiratory tract of the patient. The composition may of course contain other ingredients as needed, including other pharmaceutically active agents, other enhancers, and pharmacologically acceptable excipients such as diluents or carriers. Therefore, the therapeutic preparation of the present invention may contain only the said active compounds or it may contain other substances, such as a pharmaceutically acceptable carrier. This carrier may largely consist of particles having a diameter of less than about 10 microns so that at least 50% of the resultant powder as a whole consists of optionally agglomerated primary particles having a diameter of less than about 10 microns; alternatively the carrier may largely consist of much bigger particles ("coarse particles"), so that an "ordered mixture" may be formed between the active compounds and the said carrier. In an ordered mixture, alternatively known as an interactive or adhesive mixture, fine drug particles (in this invention, the active compounds) are fairly evenly distributed over the surface of coarse excipient particles (in this invention, the pharmaceutically acceptable carrier). Preferably in such case the active compounds are not in the form of agglomerates prior to formation of the ordered mixture. The coarse particles may have a diameter of over 20 microns, such as over 60 microns. Above these lower limits, the diameter of the coarse particles is not of critical importance so various coarse particle sizes may be used, if desired according to the practical requirements of the particular formulation. There is no requirement for the coarse particles in the ordered mixture to be of the same size, but the coarse particles may advantageously be of similar size within the ordered mixture. Preferably, the coarse particles have a diameter of 60–800 microns.

The polypeptide may be any medically or diagnostically useful peptide or protein of small to medium size, i.e. up to about 40 kD molecular weight (MW), for which systemic delivery is desired. The mechanisms of improved polypeptide absorption according to the present invention are generally applicable and should apply to all such polypeptides, although the degree to which their absorption is improved may vary according to the MW and the physico-chemical properties of the polypeptide, and the particular enhancer used. It is expected that polypeptides having a molecular weight of up to 30 kD will be most useful in the present invention, such as polypeptides having a molecular weight of up to 25 kD or up to 20 kD, and especially up to 15 kD or up to 10 kD. Any desired polypeptide may be easily tested for use in the present invention with a particular enhancer, by in vivo or in vitro assays, as described herein.

The enhancer compound used in the compositions of the present invention can be any compound which enhances the absorption of the polypeptide through the epithelium of the lower respiratory tract, and into the systemic circulation. By "enhances absorption" is meant that the amount of polypeptide absorbed into the systemic circulation in the presence of enhancer is higher than in the absence of enhancer. Preferably the amount of polypeptide absorbed is significantly higher ($p<0.05$) in the presence of enhancer. The suitability of any potential enhancer for use in the present invention may be easily assessed, by means of in vivo or in vitro assays, as described herein.

The amount of polypeptide absorbed according to the present invention is preferably at least 150% of the amount absorbed in the absence of enhancer. In preferred embodiments, absorption of polypeptide is at least doubled, more preferably tripled, and most preferably quadrupled in the presence of the enhancer, compared to in its absence.

The enhancer is preferably a surfactant such as a salt of a fatty acid, a bile salt, a bile salt derivative, an alkyl glycoside, a cyclodextrin, or a phospholipid. The enhancer may be, for example, a sodium, potassium, or organic amine salt of the fatty acid, and the fatty acid is preferably capric acid or another fatty acid of 10–14 carbon atoms. The preferred enhancer is sodium caprate. The ratio of polypeptide to enhancer will preferably vary from about 9:1 to about 1:1. Although proportions of enhancer greater than 1:1 would presumably enhance uptake as well as or better than lower proportions, it is believed that the amount of enhancer used should be no higher than necessary to achieve the desired level of enhancement, since excess enhancer may trigger unwanted side effects, such as local irritation.

Also within the invention is a method of administering systemically a pharmaceutically active polypeptide, by causing a patient to inhale the pharmaceutical composition of the invention, wherein at least 50% of the total mass of the active compounds at the point of entry to the respiratory tract of the patient consists of particles having a diameter less than or equal to about 10 microns. This is preferably accomplished by the use of an inhaler device from which the patient inhales the powder. Where the powdered composition is in the form of agglomerates of primary particles, the device is preferably configured to induce substantial deagglomeration of the agglomerates upon inhalation of the powder from the device by the patient, so that the majority of the agglomerates break down into particles having a diameter less than or equal to about 10 microns, prior to entry of the powder into the respiratory system of the patient. This deagglomeration would occur inside the device, and is typically induced by the air turbulence created in the device by the force of inhalation. Agglomerates are in general preferably not formed in the ordered mixture. In the case of an ordered mixture, the active compounds should be released from the large particles preferably upon inhalation, either by mechanical means in the inhaler device or simply by the action of inhalation, or by other means, the active compounds then being deposited in the lower respiratory tract and the carrier particles in the mouth.

The inhaler device is preferably a single dose dry powder inhaler, but may alternatively be a multi dose dry powder inhaler.

The invention also includes processes for the manufacture of a pharmaceutical composition suitable for administration by inhalation. In one such process, a solution is first provided in which are dissolved (a) a pharmaceutically active polypeptide and (b) an enhancer compound which enhances the systemic absorption of the polypeptide in the lower respiratory tract of a patient. The solvent is then removed from the solution to yield a dry solid containing the polypeptide and the enhancer, and the dry solid is pulverized to produce a powder. A second such process involves dry mixing (a) a pharmaceutically active polypeptide and (b) an enhancer compound, and micronizing the obtained mixture. Yet a third suitable process includes the steps of providing a first micronized preparation containing a polypeptide and a second micronized preparation containing an enhancer compound, and mixing the two micronized preparations together. When a carrier is to be included other than when an ordered mixture is desired, this may be added to the solution, or to the dry-mixture of the pharmaceutically active polypeptide prior to micronization, or micronised carrier may be dry mixed with the other micronised components. In producing an ordered mixture, micronised polypeptide and enhancer are mixed with a suitable carrier.

DETAILED DESCRIPTION

Some of the preferred embodiments of the invention are generally described below.

The Polypeptide

The polypeptide is preferably a peptide hormone other than insulin, such as vasopressin, vasopressin analogues, desmopressin, glucagon, corticotropin (ACTH), gonadotropin (luteinizing hormone, or LHRH), calcitonin, C-peptide of insulin, parathyroid hormone (PTH), human growth hormone (hGH), growth hormone (HG), growth hormone releasing hormone (GHRH), oxytocin, corticotropin releasing hormone (CRH), somatostatin analogs, gonadotropin agonist analogs (GnRHa), human atrial natriuretic peptide (hANP), recombinant human thyroxine releasing hormone (TRHrh), follicle stimulating hormone (FSH), and prolactin.

Other possible polypeptides include growth factors, interleukins, polypeptide vaccines, enzymes, endorphins, glycoproteins, lipoproteins, and polypeptides involved in the blood coagulation cascade, that exert their pharmacological effect systemically. It is expected that most if not all polypeptides of small to medium size, relatively high water solubility, and an isoelectric point between approximately pH 3 and pH 8 can be effectively delivered by the methods of the invention.

The Enhancer

The use of an absorption enhancer is of critical importance, as the polypeptide alone is poorly absorbed through the lung. The enhancer used can be any of a number of compounds which act to enhance absorption through the layer of epithelial cells lining the lower respiratory tract, and into the adjacent pulmonary vasculature. The enhancer can accomplish this by any of several possible mechanisms:

(1) Enhancement of the paracellular permeability of a polypeptide by inducing structural changes in the tight junctions between the epithelial cells.

(2) Enhancement of the transcellular permeability of a polypeptide by interacting with or extracting protein or lipid constituents of the membrane, and thereby perturbing the membrane's integrity.

(3) Interaction between enhancer and polypeptide which increases the solubility of the polypeptide in aqueous solution. This may occur by preventing formation of insulin aggregates (dimers, trimers, hexamers), or by solubilizing polypeptide molecules in enhancer micelles.

(4) Decreasing the viscosity of, or dissolving, the mucus barrier lining the alveoli and passages of the lung, thereby exposing the epithelial surface for direct absorption of the polypeptide.

Enhancers may function by only a single mechanism set forth above, or by two or more. An enhancer which acts by several mechanisms is more likely to promote efficient absorption of a polypeptide than one which employs only one or two.

For example, surfactants are a class of enhancers which are believed to act by all four mechanisms listed above. Surfactants are amphiphilic molecules having both a lipophilic and a hydrophilic moiety, with varying balance between these two characteristics. If the molecule is very lipophilic, the low solubility of the substance in water may limit its usefulness. If the hydrophilic part overwhelmingly dominates, however, the surface active properties of the molecule may be minimal. To be effective, therefore, the surfactant must strike an appropriate balance between sufficient solubility and sufficient surface activity.

Another surfactant property that may be of importance is the net charge of the surfactant at the pH value in the lung (approximately 7.4). At pH 7.4, some polypeptides have a negative net charge. This will result in an electrostatic repulsion between molecules, which will in turn prevent aggregation and thereby increase the solubility. If the surfactant also is negatively charged, it can interact with the polypeptide by, for example, hydrophobic interactions, and additional repulsion among the polypeptide molecules will occur. In such case an anionic surfactant will possess the additional advantage (compared to those having neutral or net positive charge at physiological pH) of enhancing absorption by helping stabilize the polypeptide in the monomeric state.

A number of different compounds potentially useful as enhancers in the methods of the invention were tested in rats, as described in Example 2 below. Other substances with known absorption-enhancing properties, or with physical characteristics which make them likely candidates for use in the method of the invention, can be readily tested by one of ordinary skill in that in vivo assay, or alternatively in the in vitro assay described in Example 1.

It is possible that a combination of two or more enhancer substances also gives satisfactory results. The use of such a combination in the method of the invention is considered to be within the invention.

An enhancer useful in the methods of the invention will combine effective enhancement of polypeptide absorption with (1) lack of toxicity in the concentrations used and (2) good powder properties, i.e., lack of a sticky or waxy consistency in the solid state. Toxicity of a given substance can be tested by standard means, such as by the MTT assay, for example as described in Int. J. Pharm., 65 (1990), 249–259. The powder properties of a given substance may be ascertained from published data on the substance, or empirically.

One very promising type of enhancer is the salt of a fatty acid. It has been found that the sodium salt of saturated fatty acids of carbon chain length 10 (i.e., sodium caprate), 12 (sodium laurate) and 14 (sodium myristate) perform well in the method of the invention. The potassium and lysine salts of capric acid have also been found to be effective in the method of the invention. If the carbon chain length is shorter than about 10, the surface activity of the surfactant may be too low, and if the chain length is longer than about 14, decreased solubility of the fatty acid salt in water limits its usefulness.

Most preferably in the present invention the substance which enhances the absorption of polypeptide in the lower respiratory tract is sodium caprate.

Different counterions may change the solubility of the saturated fatty acid salt in water, such that an enhancer having a carbon length other than 10–14 would prove even more advantageous than the enhancers specifically mentioned hereinabove. Salts of unsaturated fatty acids may also be useful in the present invention since they are more water soluble than salts of saturated fatty acids, and can therefore have a longer chain length than the latter and still maintain the solubility necessary for a successful enhancer of polypeptide absorption.

All of the bile salts and bile salt derivatives tested (sodium salts of ursodeoxycholate, taurocholate, glycocholate, and taurodihydrofusidate) effectively enhance polypeptide absorption in the lung.

Phospholipids were also tested as enhancers. It was found that a single-chain phospholipid (lysophospatidylcholine) was an effective enhancer, while two double-chain phospholipids (dioctanoylphosphatidylcholine and didecanoylphosphatidylcholine) were not. This may be explained by the fact that the double-chain phospholipids are much less soluble in water than their single-chain counterparts; however, it is reasonable to expect that double-chain phospholipids of shorter chain length, having greater water-solublility than their longer chain counterparts, will be of use as enhancers in the present invention so that both single- and double-chain phospholipids may be used.

One glycoside, octylglucopyranoside, was tested as an enhancer in the present invention and was found to have some absorption enhancing properties. Other alkyl glycosides, such as thioglucopyranosides and maltopyranosides would also be expected to exhibit absorption enhancing properties in the methods of the present invention.

The cyclodextrins and derivatives thereof effectively enhance nasal absorption, and may function similarly in the lung. Dimethyl-$\beta$-cyclodextrin has been tested and was found to have an absorption enhancing effect.

Other potentially useful surfactants are sodium salicylate, sodium 5-methoxysalicylate, and the naturally occurring surfactants such as salts of glycyrrhizine acid, saponin glycosides and acyl carnitines.

For ionic enhancers (e.g., the anionic surfactants described above), the nature of the counterion may be important. The particular counterion selected may influence the powder properties, solubility, stability, hygroscopicity, and local/systemic toxicity of the enhancer or of any formulation containing the enhancer. It may also affect the stability and/or solubility of the polypeptide with which it is combined. In general, it is expected that monovalent metallic cations such as sodium, potassium, lithium, rubidium, and cesium will be useful as counterions for anionic enhancers. Ammonia and organic amines form another class of cations that is expected to be appropriate for use with anionic enhancers having a carboxylic acid moiety. Examples of such organic amines include ethanolamine, diethanolamine, triethanolamine, 2-amino-2-methylethylamine, betaines, ethylenediamine, N,N-dibensylethylenetetraamine, arginine, hexamethylenetetraamine, histidine, N-methylpiperidine, lysine, piperazine, spermidine, spermine and tris(hydroxymethyl) aminomethane.

Since effective enhancement of polypeptide absorption in the lung was observed for a number of the enhancers tested, it is expected that many more will be found which also function in this manner. Starch microspheres effectively enhance the bioavailability of polypeptide delivered via the nasal membranes and were tested as an enhancer in the methods of the invention. Although they proved to be of little use for delivery via the pulmonary route in the animal model utilized herein, it is thought that this was mainly due to technical difficulties which, if overcome, may lead to successful delivery via the pulmonary route.

Chelators are a class of enhancers that are believed to act by binding calcium ions. Since calcium ions help maintain the dimensions of the space between cells and additionally reduce the solubility of a polypeptide, binding of these ions would in theory both increase the solubility of polypeptides, and increase the paracellular permeability of polypeptides.

Although one chelator tested, the sodium salt of ethylenediaminetetraacetic acid (EDTA), was found to be ineffective in enhancing absorption of insulin in the rat model tested, other calcium ion-binding chelating agents may prove to be more useful.

Proportions of Polypeptide and Enhancer

The relative proportions of polypeptide and enhancer may be varied as desired. Sufficient enhancer must be present to permit efficient absorption of the inhaled polypeptide; however, the amount of enhancer should be kept as low as possible in order to minimize the risk of adverse effects caused by the enhancer. Although each particular polypeptide/enhancer combination must be tested to determine the optimal proportions, it is expected that to achieve acceptable absorption of the polypeptide, more than 10% of the polypeptide/enhancer mixture must be enhancer; for most types of enhancers, the proportion of enhancer should be more than 15% or more than 20% and will preferably be between 25% and 50%. The preferred ratio for each polypeptide/enhancer (or polypeptide/enhancer/diluent) combination can be readily determined by one of ordinary skill in the art of pharmacology by standard methods, based on such criteria as efficient, consistent delivery of the optimal dosage, minimization of side effects, and acceptable rate of absorption.

No further ingredients are needed for the action of the preparation, but may be included if desired. For example, the amount of powder which constitutes a single dose of a given polypeptide/surfactant combination could be increased (e.g., for use in an inhaler apparatus which by design requires a large powder volume per dose) by diluting the powder with pharmaceutically acceptable diluents. Other additives may be included to facilitate processing or to improve the powder properties or stability of the preparation. A flavouring agent could be added so that the proportion of the powder which is inevitably deposited in the mouth and throat would serve to give the patient positive feedback that a dose had been delivered from the inhaler device. Any such additive should have the following properties: (a) it is stable and does not disadvantageously affect the stability of the polypeptide and enhancer; (b) it does not disadvantageously interfere with absorption of the polypeptide; (c) it has good powder properties, as that term is understood in the pharmaceutical arts; (d) it is not hygroscopic; and (e) it has no adverse effects in the airways in the concentrations used. Useful types of such additives include mono-, di-, and polysaccharides, sugar alcohols, and other polyols: for example, lactose, glucose, raffinose, melezitose, lactitol, maltitol, trehalose, sucrose, mannitol, and starch. As reducing sugars such as lactose and glucose have a tendency to form complexes with proteins, non-reducing sugars such as raffinose, melezitose, lactitol, maltitol, trehalose, sucrose, mannitol and starch may be preferred additives for use in the present invention. Such additives may constitute anywhere from 0% (i.e., no additive) to nearly 100% of the total preparation.

In a preferred embodiment, this invention provides a therapeutic preparation of a pharmaceutically active polypeptide and a substance which enhances the absorption of said polypeptide in the lower respiratory tract, which preparation is in the form of a dry powder preparation suitable for inhalation of which at least 50% by mass consists of (a) particles having a diameter of less than about 10 microns or (b) agglomerates of said particles; in another preferred embodiment, the invention provides a therapeutic preparation comprising a pharmaceutically active polypeptide, a substance which enhances the absorption of polypeptide in the lower respiratory tract, and a pharmaceutically acceptable carrier, which preparation is in the form of a dry powder suitable for inhalation of which at least 50% by mass consists of (a) particles having a diameter of less than about 10 microns, or (b) agglomerates of said particles; and in a further preferred embodiment this invention provides a therapeutic preparation comprising active compounds (A) a pharmaceutically active polypeptide and (B) a substance which enhances the absorption of said polypeptide in the lower respiratory tract, wherein at least 50% of the total mass of active compounds (A) and (B) consists of particles having a diameter of less than about 10 microns, and a pharmaceutically acceptable carrier, which preparation is in the form of a dry powder preparation suitable for inhalation in which an ordered mixture may be formed between the active compounds and the pharmaceutically acceptable carrier.

The described powder preparation could be manufactured in several ways, using conventional techniques. In many cases, the purified polypeptide can be obtained from commercial sources. Alternatively, the polypeptide of interest can be purified from a naturally occurring source using standard biochemical techniques, or can be obtained by expression of prokaryotic or eukaryotic cells genetically engineered to contain a nucleotide sequence which encodes the polypeptide and has appropriate expression control sequences linked thereto (including a transgenic animal engineered to manufacture the desired peptide or protein, for example in its milk). Such methods are standard in the art (e.g., see Sambrook et al., Molecular Cloning: A Laboratory Manual; Cold Spring Harbor Laboratory Press, Cold Spring Harbor, N.Y., 1989). Peptides (i.e., polypeptides having 30 or fewer amino acid residues) can be readily synthesized by known chemical means.

Absorption enhancers as described above are also generally available from commercial sources, or can be manufactured using published methods. For ionic enhancers, the counterion associated with the enhancer can be replaced with another, if desired, using standard ion exchange techniques.

In manufacturing of the described powder preparation it will in general be necessary to micronize the powder in a suitable mill, e.g. a jet mill, at some point in the process, in order to produce primary particles in a size range appropriate for maximal deposition in the lower respiratory tract (i.e., under 10 $\mu$m). For example, one can dry mix polypeptide and enhancer powders, and then micronize the substances together; alternatively, the substances can be micronized separately, and then mixed. Where the compounds to be mixed have different physical properties such as hardness and brittleness, resistance to micronisation varies and they may require different pressures to be broken down to suitable particle sizes. When micronised together, therefore, the obtained particle size of one of the components may be unsatisfactory. In such case it would be advantageous to micronise the different components separately and then mix them.

It is also possible first to dissolve the components in a suitable solvent, e.g. water, to obtain mixing on the molecular level. This procedure also makes it possible to adjust the pH-value to a desired level, for instance to improve absorption of the polypeptide. The pharmaceutically accepted limits of pH 3.0 to 8.5 for inhalation products must be taken into account, since products with a pH outside these limits may induce irritation and constriction of the airways. To obtain a powder, the solvent must be removed by a process which retains the polypeptide's biological activity. Suitable drying methods include vacuum concentration, open drying, spray drying, and freeze drying. Temperatures over 40° C. for more than a few minutes should generally be avoided, as some degradation of certain polypeptides may occur. Following the drying step, the solid material can, if necessary, be ground to obtain a coarse powder, then, if necessary, micronized.

If desired, the micronized powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range. Where an ordered mixture is desired, the active compound may be processed, for example by micronisation, in order to obtain, if desired, particles within a particular size range. The carrier may also be processed, for example to obtain a desired size and desirable surface properties, such as a particular surface to weight ratio, or a certain ruggedness, and to ensure optimal adhesion forces in the ordered mixture. Such physical requirements of an ordered mixture are well known, as are the various means of obtaining an ordered mixture which fulfills the said requirements, and may be determined easily by the skilled person according to the particular circumstances.

A preferred inhalation apparatus would have the following design characteristics: protection of the powder from moisture and no risk of occasional large doses; in addition as many as possible of the following are desired: protection of the powder from light; high respirable fraction and high lung deposition in a broad flow rate interval; low deviation of dose and respirable fraction; low retention of powder in the mouthpiece—this is particularly important for a multi-dose inhaler, where polypeptide retained in the mouthpiece could degrade and then be inhaled together with subsequent doses; low adsorption to the inhaler surfaces; flexibility in dose size; and low inhalation resistance. The inhaler is preferably a single dose inhaler although a multi dose inhaler, such as a multi dose, breath actuated, dry powder inhaler for multiple use, may also be employed. Peferably the inhaler used is a unit dose, breath actuated, dry powder inhaler for single use.

A number of dry powder formulations containing a polypeptide and various enhancers have been prepared and tested in an in vivo assay, and are described below. Also described is an in vitro assay useful for testing polypeptide/enhancer combinations.

EXAMPLE 1

In Vitro Method of Determining Usefulness of Particular Polypeptides for the Present Invention.

A standard in vitro assay utilizing an epithelial cell line, CaCo-2 (available through the American Type Culture Collection (ATCC), Rockville, Md., USA), has been developed to assess the ability of various enhancer compounds to promote transport of markers across an epithelial cell monolayer, as a model for the epithelial cell layer which functions in the lung to separate the alveolus from the pulmonary blood supply.

In this assay, the enhancer and polypeptide or other marker are dissolved in aqueous solution at various proportions and/or concentrations, and applied to the apical side of the cell monolayer. After 60 min incubation at 37° C. and 95% RH (relative humidity), the amount of the marker on the basolateral side of the cells is determined, e.g., by use of a radioactively labelled marker.

Figure 1:
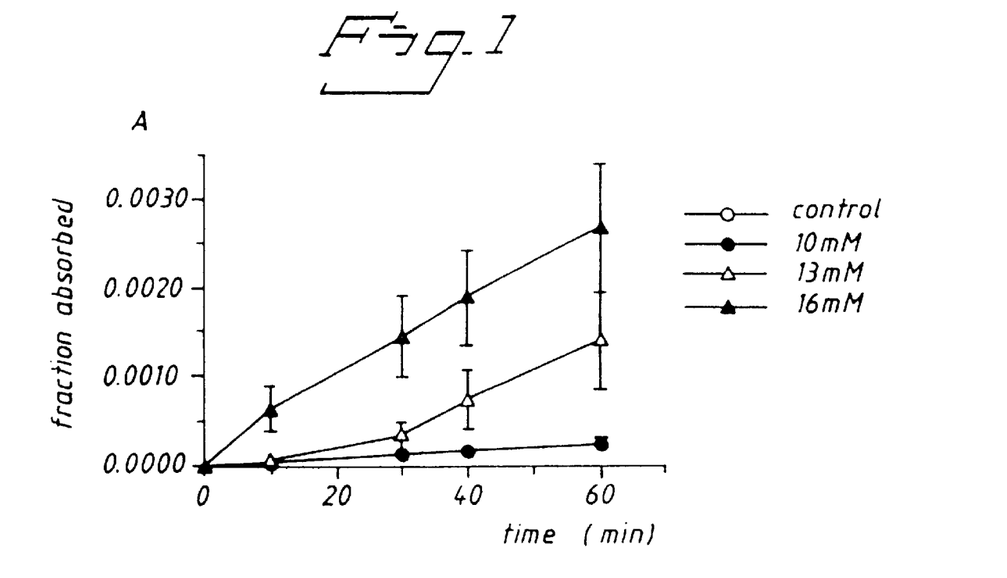
FIG. 1 is a graph illustrating the effects of different concentrations of sodium caprate enhancer on the transport of a marker compound (mannitol) through a monolayer of cultured epithelial cells.
Figure 2:
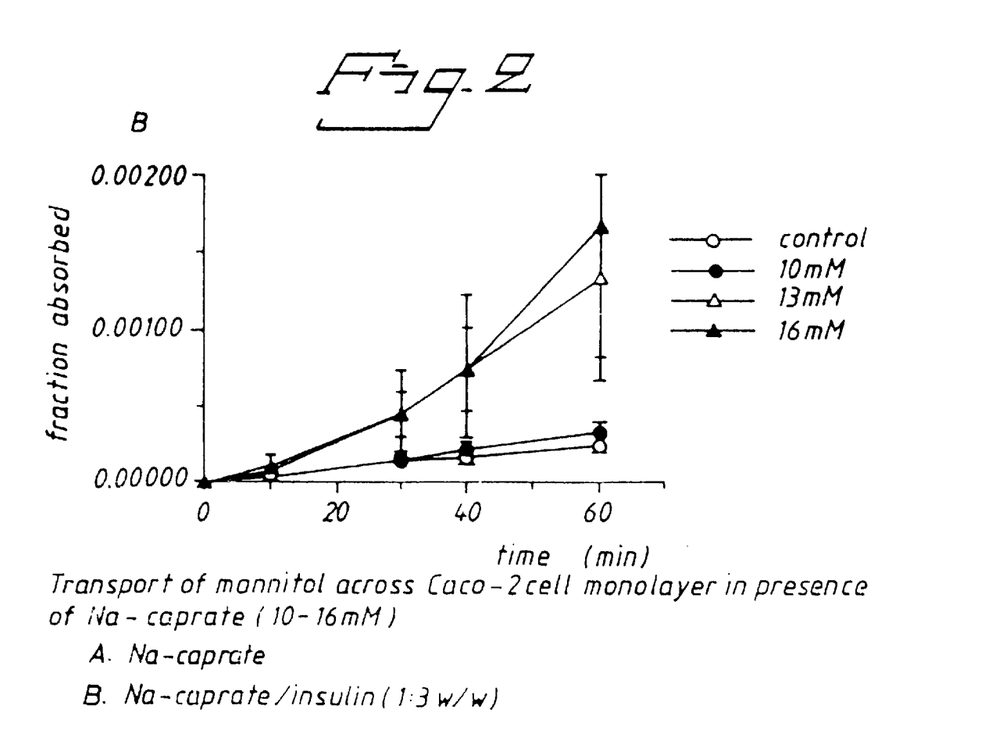
FIG. 2 is a graph illustrating the effects of different concentrations of sodium caprate enhancer on the transport of a marker compound (mannitol) through a monolayer of cultured epithelial cells, in the presence of a polypeptide (sodium caprate:polypeptide 1:3 by weight).

For the enhancer tested, sodium caprate, the amount of marker (mannitol, MW 360) which appears on the basolateral side is dependent upon the concentration of enhancer used, at least up to 16 mM sodium caprate (FIG. 1). This is true even when the polypeptide insulin is added to the enhancer/mannitol mixture (1:3 sodium caprate:insulin, by weight) (FIG. 2). This concentration of sodium caprate (16 mM) was also found to promote absorption across the cell monolayer of two low molecular weight peptides, insulin (MW 5734) and vasopressin (MW 1208). The amount of insulin which passed across the monolayer doubled in the presence of 16 mM sodium caprate, compared to the amount in the absence of any enhancer; the amount of vasopressin which was absorbed across the monolayer increased 10–15 times compared to the amount in the absence of any enhancer.

In contrast, no increase in transport rate was observed for larger proteins such as cytochrome C (MW 12,300), carbonic anhydrase (MW 30,000) and albumin (MW 69,000) when tested at up to 16 mM sodium caprate. It is expected that at higher concentrations of sodium caprate, the permeability of the cells will be further increased, permitting the transport of larger polypeptides; however, the potential cytotoxicity of sodium caprate may prevent the use of substantially higher concentrations of this particular enhancer.

Other enhancers may permit transportation of larger polypeptides; these may also be tested in this in vitro model of epithelial cell permeability, which can be used as a screening tool for rapidly testing any desired polypeptide/enhancer combination for usefulness in the methods of the invention.

EXAMPLE 2

Method for Selecting Enhancers Useful for the Present Invention

Each of the compounds listed in Table I was tested for its ability to enhance uptake of a polypeptide (insulin) in a rat model. The results with insulin are taken as indicative of the enhancer's potential for enhancement of absorption of other polypeptides.

Various forms of insulin were employed in the different trials: recombinant human, semisynthetic human or bovine. Each formulation was prepared as above, drying and processing the insulin/enhancer or insulin/enhancer/lactose solution to produce an inhalable powder. The powder was administered to rats by inhalation, and the blood glucose levels of the rats were subsequently monitored as a measure of insulin uptake. These levels were compared to the corresponding values obtained from rats which had inhaled insulin formulations without enhancer.

The same in vivo model system could be used to test any given peptide or protein for usefulness in the methods of the invention, by delivering by the same inhalation method a formulation containing the desired peptide or protein combined with an enhancer, and assaying for the concentration of the desired peptide or protein in the systemic circulation of the test animal (e.g., by standard immunoassays or biochemical assays as appropriate for the given peptide or protein).

TABLE I

| Substance | Enhancer: Insulin: lactose | Effect |
|---|---|---|
| Octylglucopyranoside | 4:4:92 | (+) |
| Sodium ursodeoxycholate | 4:4:92 | + |
| Sodium taurocholate | 4:4:92 | + |
| Sodium glycocholate | 4:4:92 | + |
| Lysophosphatidylcholine | 4:4:92 | + |
| Dioctanoylphosphatidylcholine | 2:4:94 | (+) |
| Dioctanoylphosphatidylcholine | 4:4:94 | − |
| Sodium tarodihydrofusidate | 2:4:94 | + |
| Sodium caprylate | 25:75:0 | − |
| Sodium caprate | 10:90:0 | (+) |

TABLE I-continued

| Substance | Enhancer: Insulin: lactose | Effect |
| --- | --- | --- |
| Sodium caprate | 17.5:82.5:0 | (+) |
| Sodium caprate | 25:75:0 | + |
| Potassium oleate | 4:4:92 | + |
| Sodium laurate | 25:75:0 | + |
| Potassium oleate | 4:4:92 | + |
| Potassium caprate | 27:73:0 | + |
| Lysine caprate | 35:65:0 | + |
| Sodium myristate | 30:70:0 | + |
| Dimethyl-β-cyclodextrin | 75:25:0 | + |

+strong effect, i.e. a significant decrease in blood glucose level
(+)moderate effect
−no or very small effect EXAMPLE 3
Therapeutic Preparation According to the Invention Human growth hormone (hGH, MW 22 kD, source Humatrope from Lilly, 3 parts) was mixed with sodium caprate (1 part). The mixture was milled in a Retsch mechanical mill to a particle size of mass median diameter 6.7 μm.

The resultant powder was administered intratraceally in rats and the uptake of hGH compared with that of a powder, MMD 9.6 μm, comprising hGH and mannitol in the same proportions and prepared in the same way as above.

The results indicated an improvement in the uptake of hGH in the formulation including sodium caprate, compared with the uptake in the formulation without enhancer.

EXAMPLE 4
Preparation Containing the Polypeptide Insulin

Insulin is herein used as indicative of other polypeptides according to the present invention.

Biosynthetic human insulin (53 g) was micronised in an Airfilco Jet Mill (Trade Mark, Airfilco Process Plant Limited), with pressurised nitrogen (feed pressure 7 bar, chamber pressure 5 bar), to a mass median diameter of 2.4 micrometers.

Sodium caprate (170 g) was micronised in an Airfilco Jet Mill (TM), with pressurised nitrogen (feed pressure 5 bar, chamber pressure 3 bar), to a mass median diameter of 1.6 micrometers.

The micronised biosynthetic human insulin (45 g) and sodium caprate (14.26 g) were dry mixed according to the following procedure: Half of the insulin was added to a mixing device comprising a mixing cylinder of volume 4.4 litres divided, by a sieve of width 1 mm, into two compartments, with a metal ring in each compartment to aid mixing and stirring. The sodium caprate and finally the rest of the insulin, were added. The mixing cylinder was closed, turned 180 degrees, and mounted in a motorised shaking apparatus. The motor was turned on and shaking continued for approximately two minutes, until all the insulin and sodium caprate had passed through the sieve. The motor was turned off and the mixing cylinder turned 180 degrees, again mounted on the shaking apparatus and shaking was again effected until all the powder had passed through the sieve. This procedure was repeated a further eight times to give a total mixing time of approximately 20 minutes.

The preparation so obtained was administered to 5 dogs by inhalation, at a dosage level of 1 U./kg, and the plasma insulin level determined at various time points after administration.

The results obtained were compared with the plasma insulin levels obtained when biosynthetic insulin, micronised as above to a mass median diameter of 2.4 micrometers, were administered to five dogs in the same way and at the same dosage levels, and with the plasma insulin levels obtained when a therapeutic preparation of insulin and sodium caprate in a ratio of 90:10 was administered to five dogs in the same way and at the same dosage levels as above. In this case the therapeutic preparation was prepared as follows: Human semisynthetic insulin was gel filtrated to reduce the zinc content from 0.52% to 0.01% relative to content of insulin. Insulin (4.5 g) and sodium caprate (0.5 g) were dissolved in water (232 ml). The solution was stirred until clear and the pH adjusted to 7.0. The solution was concentrated by evaporation at 37° C. over a period of about two days. The obtained solid cake was crushed, and sieved through a 0.5 mm sieve, and the resultant powder micronised through a jet mill to particles with a mass median diameter of 3.1 micrometers.

Figure 3:
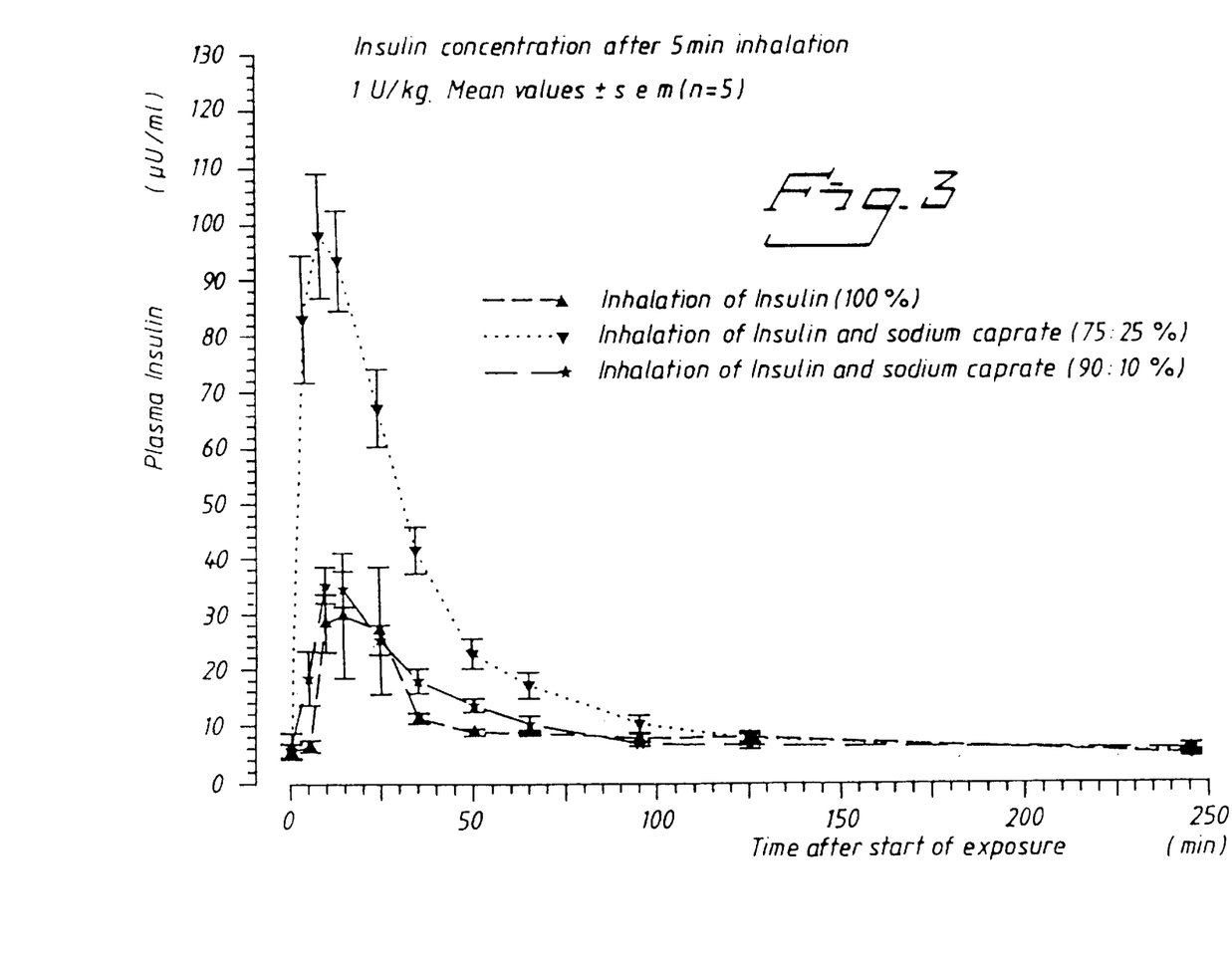
FIG. 3 is a graph of plasma polypeptide concentration as a function of time after inhalation of the polypeptide alone, the polypeptide with sodium caprate in a ratio of 90:10, and the polypeptide with sodium caprate in a ratio of 75:25.

The results of these comparisons are presented in FIG. 3 ($p=0.0147$ for the difference between 75:25 and 100:0). The results demonstrate some improvement in the bioavailability of insulin with the 90:10 formulation, and a dramatic improvement in the bioavailability of insulin with the 75:25 preparation including sodium caprate, as compared to insulin alone.

What is claimed is:

1. A process for the manufacture of a pharmaceutical composition suitable for administration by oral inhalation from a dry powder inhaler device, comprising providing a solution in which are dissolved (a) a pharmaceutically active polypeptide, and (b) an enhancer compound which enhances the systemic absorption of the polypeptide in the lower respiratory tract of a patient;

removing the solvent from said solution to yield a dry solid comprising said polypeptide and said enhancer compound;

pulverizing said dry solid to produce a powder, wherein at least 50% of the total mass of said powder is in the form of primary particles having a diameter less than about 10 microns, said primary particles being optionally agglomerated; and loading the powder into a dry powder inhaler device adapted for inhalation through the mouth.

2. A process as claimed in claim 1, comprising the step of forming the primary particles into agglomerates.

3. A process as claimed in claim 1, wherein said polypeptide is selected from the group consisting of vasopressin, vasopressin analogues, desmopressin, glucagon, corticotropin, gonadotropin, calcitonin, C-peptide of insulin, parathyroid hormone, human growth hormone, growth hormone, growth hormone releasing hormone, oxytocin, corticotropin releasing hormone, a somatostatin analogue, a gonadotropin agonist analogue, atrial natriuretic peptide, thyroxine releasing hormone, follicle stimulating hormone, prolactin; an interleukin, a growth factor, a polypeptide vaccine, an enzyme, an endorphin, a glycoprotein, a lipoprotein, and a polypeptide involved in the blood coagulation cascade, that exerts its pharmacological effect systemically.

4. A process as claimed in claim 1, wherein said polypeptide has a molecular weight of up to 20 kD.

5. A process as claimed in claim 1, wherein said enhancer compound is selected from the group consisting of an anionic surfactant, a cationic surfactant, a phospholipid, an alkyl glycoside, a cyclodextrin, a salt of capric acid, and a sodium, potassium or organic amine salt of a fatty acid.

6. A process as claimed in claim 1, wherein said enhancer compound is selected from the group consisting of dimethyl- β-cyclodextrin, dioctanoylphosphatidylcholine, lysophosphatidylcholine, and a salt of caprate, laurate, oleate, or myristate.

7. A process as claimed in claim 1, wherein the enhancer compound constitutes between 20% and 50% by weight of said dry solid.

8. A process as claimed in claim 1, wherein at least 90% of the total mass of said powder is in the form of said primary particles having a diameter less than about 10 microns.

9. A process as claimed in claim 1, wherein the solution further comprises a dissolved pharmaceutically acceptable carrier.

10. A process as claimed in claim 1, comprising the additional step of mixing particles of a pharmaceutically acceptable carrier with said powder.

11. A process as claimed in claim 10, wherein the carrier particles have a diameter less than about 10 microns.

12. A process as claimed in claim 10, wherein the carrier particles have a diameter between 60 and 800 microns.

13. A process as claimed in claim 1, wherein said enhancer compound is a bile salt.

14. A process as claimed in claim 1, wherein said enhancer compound is a salt of ursodeoxycholate, taurocholate, glycocholate, or taurodihydrofusidate.

15. A process as claimed in claim 1, wherein the solvent is removed by spray drying.

16. A process as claimed in claim 1, wherein the solvent is removed by vacuum concentration.

17. A process as claimed in claim 1, wherein the solvent is removed by open drying.

18. A process for the preparation of a pharmaceutical composition suitable for administration by oral inhalation from a dry powder inhaler device, comprising
   dry mixing (a) a pharmaceutically active polypeptide, and (b) an enhancer compound which enhances the absorption of the polypeptide in the lower respiratory tract of a patient,
   micronizing the obtained mixture to produce a micronized mixture, wherein at least 50% of the total mass of said micronized mixture is in the form of primary particles having a diameter less than about 10 microns, said primary particles being optionally agglomerated; and
   loading the micronized mixture into a dry powder inhaler device adapted for inhalation through the mouth.

19. A process as claimed in claim 18, comprising the step of forming the primary particles into agglomerates.

20. A process as claimed in claim 18, wherein said polypeptide is selected from the group consisting of vasopressin, a vasopressin analogue, desmopressin, glucagon, corticotropin, gonadotropin, calcitonin, C-peptide of insulin, parathyroid hormone, human growth hormone, growth hormone, growth hormone releasing hormone, oxytocin, corticotropin releasing hormone, a somatostatin analogue, a gonadotropin agonist analogue, atrial natriuretic peptide, thyroxine releasing hormone, follicle stimulating hormone, prolactin, an interleukin, a growth factor, a polypeptide vaccine, an enzyme, an endorphin, a glycoprotein, a lipoprotein, and a polypeptide involved in the blood coagulation cascade, that exerts its pharmacological effect systemically.

21. A process as claimed in claim 18, wherein said polypeptide has a molecular weight of up to 20 Kd.

22. A process as claimed in claim 18, wherein said enhancer compound is selected from the group consisting of an anionic surfactant, a cationic surfactant, a phospholipid, an alkyl glycoside, a cyclodextrin, a salt of capric acid, and a sodium, potassium or organic amine salt of a fatty acid.

23. A process as claimed in claim 18, wherein said enhancer compound is selected from the group consisting of dimethyl-β-cyclodextrin, dioctanoylphosphatidylcholine, lysophosphatidylcholine, and a salt of caprate, laurate, oleate, or myristate.

24. A process as claimed in claim 18, wherein said enhancer compound constitutes between 20% and 50% by weight of said mixture.

25. A process as claimed in claim 18, wherein at least 90% of the total mass of said micronized mixture is in the form of said primary particles having a diameter less than about 10 microns.

26. A process as claimed in claim 18, wherein a pharmaceutically acceptable carrier is mixed with the polypeptide and enhancer compound in the dry mixing step.

27. A process as claimed in claim 18, comprising the additional step of mixing particles of a pharmaceutically acceptable carrier with the micronized mixture.

28. A process as claimed in claim 27, wherein the carrier particles have a diameter less than about 10 microns.

29. A process as claimed in claim 27, wherein the carrier particles have a diameter between 60 and 800 microns.

30. A process as claimed in claim 18, wherein said enhancer compound is a bile salt.

31. A process as claimed in claim 18, wherein said enhancer compound is a salt of ursodeoxycholate, taurocholate, glycocholate, or taurodihydrofusidate.

32. A process as claimed in claim 18, wherein the solvent is removed by spray drying.

33. A process as claimed in claim 18, wherein the solvent is removed by vacuum concentration.

34. A process as claimed in claim 18, wherein the solvent is removed by open drying.

35. A process for the manufacture of a pharmaceutical composition suitable for administration by oral inhalation from a dry powder inhaler device, comprising
   providing a first micronized preparation comprising a polypeptide and a second micronized preparation comprising an enhancer compound which enhances the absorption of the polypeptide in the lung of a patient;
   mixing said first and second micronized preparations to form a powder mixture, wherein at least 50% of the total mass of said polypeptide and enhancer in said powder mixture is in the form of primary particles having a diameter less than about 10 microns, said primary particles being optionally agglomerated; and
   loading the powder mixture into a dry powder inhaler device adapted for inhalation through the mouth.

36. A process as claimed in claim 35, comprising the step of forming the primary particles into agglomerates.

37. A process as claimed in claim 35, wherein said polypeptide is selected from the group consisting of vasopressin, a vasopressin analogue, desmopressin, glucagon, corticotropin, gonadotropin, calcitonin, C-peptide of insulin, parathyroid hormone, growth hormone, growth hormone releasing hormone, oxytocin, corticotropin releasing hormone, a somatostatin analogue, a gonadotropin agonist analogue, atrial natriuretic peptide, thyroxine releasing hormone, follicle stimulating hormone, prolactin, an interleukin, a growth factor, a polypeptide vaccine, an enzyme, an endorphin, a glycoprotein, a lipoprotein, and a polypeptide involved in the blood coagulation cascade, that exerts its pharmacological effect systemically.

38. A process as claimed in claim 35, wherein said polypeptide has a molecular weight of up to 20 kD.

39. A process as claimed in claim 35, wherein said enhancer compound is selected from the group consisting of an anionic surfactant, a cationic surfactant, a phospholipid, an alkyl glycoside, a cyclodextrin, a salt of capric acid, and a sodium, potassium or organic amine salt of a fatty acid.

40. A process as claimed in claim 35, wherein said enhancer compound is selected from the group consisting of dimethyl-β-cyclodextrin, dioctanoylphosphatidylcholine, lysophosphatidylcholine, and a salt of caprate, laurate, oleate, or myristate.

41. A process as claimed in claim 35, wherein said enhancer compound constitutes between 20% and 50% by weight of said mixture.

42. A process as claimed in claim 35, further comprising the step of combining said powder mixture with coarse particles of a pharmaceutically acceptable carrier to form an ordered mixture, said coarse particles having a diameter between 60 and 800 microns.

43. A process as claimed in claim 35, wherein at least 90% of the total mass of said polypeptide and enhancer is in the form of said primary particles having a diameter less than about 10 microns.

44. A process as claimed in claim 35, wherein the powder mixture additionally comprises micronized particles of a pharmaceutically acceptable carrier.

45. A process as claimed in claim 35, wherein said enhancer compound is a bile salt.

46. A process as claimed in claim 35, wherein said enhancer compound is a salt of ursodeoxycholate, taurocholate, glycocholate, or taurodihydrofusidate.

47. A process as claimed in claim 35, wherein the solvent is removed by spray drying.

48. A process as claimed in claim 35, wherein the solvent is removed by vacuum concentration.

49. A process as claimed in claim 35, wherein the solvent is removed by open drying.

* * * * *